United States Patent
Axelgaard et al.

(10) Patent No.: US 6,767,632 B2
(45) Date of Patent: Jul. 27, 2004

(54) DERMAL FASTENER

(75) Inventors: Jens Axelgaard, Fallbrook, CA (US);
James J. Perrault, Vista, CA (US);
Steve Heard, Escondido, CA (US);
Solomon E. Shenkute, San Diego, CA (US)

(73) Assignee: Axelgaard Manufacturing Company, Ltd., Fallbrook, CA (US)

( * ) Notice: Subject to any disclaimer, the term of this patent is extended or adjusted under 35 U.S.C. 154(b) by 0 days.

(21) Appl. No.: 10/462,862

(22) Filed: Jun. 16, 2003

(65) Prior Publication Data

US 2004/0097798 A1 May 20, 2004

Related U.S. Application Data

(63) Continuation-in-part of application No. 10/256,653, filed on Sep. 27, 2002.

(51) Int. Cl.[7] .......................... B32B 7/12; B32B 27/28; B32B 27/30
(52) U.S. Cl. .............................. 428/355 RA; 428/343; 428/354; 428/355 R; 428/355 EN; 428/355 AC
(58) Field of Search ................................. 428/343, 354, 428/355 R, 355 RA, 355 EN, 355 AC, 500, 523

(56) References Cited

U.S. PATENT DOCUMENTS

| 6,025,017 A | * | 2/2000 | Roth .......................... 427/146 |
| 6,040,040 A | * | 3/2000 | Rainbow .................... 428/32.6 |
| 6,263,226 B1 | | 7/2001 | Axelgaard et al. |

* cited by examiner

Primary Examiner—Philip Tucker
Assistant Examiner—Michael J Feely
(74) Attorney, Agent, or Firm—Walter A. Hackler

(57) ABSTRACT

A dermal fastener includes a first adhesive for adherence to an article and a second adhesive for adherence to skin. The second adhesive is a non-liquid water containing film including an organic polymer plasticized with a polyhydric alcohol with the organic polymer being derived from a monomeric mixture including from about 2 to about 30 pph acrylic acid to about 1 to about 30 pph of a glycolvinylether and about 0.01 to about 1.5 pph of a crosslinking agent. The first and second adhesives may also be disposed on opposite sides of a membrane if partition of fluid components in the adhesives is desired.

28 Claims, 2 Drawing Sheets

DERMAL FASTENER

The present application is a continuation-in-part of U.S. Ser. No. 10/256,653 filed Sep. 27, 2002.

The present invention generally relates to multi-layered adhesives and is more specifically directed to a dermal fastener for removably adhering an article to skin.

The dermal fastener in accordance with the present invention is suitable for the adhesion of various articles to the skin such as, for example, but not limited to, clothing, bras, surgical gowns, gloves, stockings, costumes, or medical devices such as intravenous catheters and nasal gastric tubes which may be temporarily affixed to an individual.

The dermal fastener is also suitable for use with prostheses such as breast replacements or other attachments, including wigs, mustaches, and the like. It is also suitable for the temporary attachment of various heat and cold packs for the application to the body for pain relief or to reduce swelling.

As hereinabove noted, the application of costumes would also include the attachment of facemasks and jewelry such as earrings, eyewear, such as spectacles, in addition to electronic devices, such as, for example, hearing aids, or devices utilized to monitor or control body function.

Another area of employment is the attachment of absorption devices such as, for example, feminine napkins and diapers. Still other articles to be attached to the skin through the use of the adhesive in accordance with the present invention would include ostomy and other drainage devices.

The present invention provides for a non-drying dermal fastener which provides secure attachment with no skin irritation, is removable from the skin without leaving significant residue thereon and can be repositioned and reapplied to the skin.

SUMMARY OF THE INVENTION

A dermal fastener in accordance with the present invention includes a first adhesive disposed for adherence to an article and a second adhesive for adherence to skin. The first adhesive may be formulated to permanently or removably adhere to the article and the second adhesive is formulated to removably adhere to the skin.

Another embodiment of the present invention includes a membrane, a first adhesive disposed on one side of the membrane for adherence to an article and a second adhesive disposed on another side of the membrane for adherence to skin preferable in the form of a film including an adhesive composition which comprises an organic polymer plasticized with a polyhydric alcohol, e.g., glycerol or other humectant.

Suitable organic polymers useful in the adhesive composition utilized in the fastener of the present invention include copolymers derived from the polymerization of acrylic acid and a glycol vinylether. Such copolymer may further include the following comonomers: 2-acrylamido propane sulfonic acid, methylene-bisacrylamide and acryloxyethyl dimethyl ammonium chloride and other cationic acrylic esters.

The adhesive composition may also include an aldehyde reactant such as, but not limited to, hydrogen peroxide, 2-hydroxyethylethylene urea (HEU) or L-arginine hydrochloride.

The precursor to said adhesive composition is copolymerized to yield a film having suitable adhesive properties and for use as a dermal fastener adhesive in the presence of an ultraviolet sensitive curing agent such as 2-hydroxy-2methyl-1-phenyl-propan-2-one (available as Darocure 1173®), 4-2-hydroxyethoxy)-phenyl-(2-hydroxy-2-phenyl-(2-hydroxy-2-propyl)ketone (available as Darocure 2959®), or 2,2-dimethoxy-2-phenylacetophenone(available as Irgacure® 651) 1-[4-(2-Hydroxyethoxy)-phenyl]-2-hydroxy-2-methyl-1-propane-1-one (as available as Irgacure® 2959) and trimethyl benzoyldiphenylphosphine oxide (available as Esacure DP250) or 1-hydroxycyclohexylphenyl ketone (available as Irgacure 184.) (Other initiators are disclosed in U.S. Pat. Nos. 5,800,685, 6,115,625 cited above). These patents are incorporated herewith in their entirety by this specific reference thereto.

In one embodiment of the present invention, the fastener includes a second adhesive having a first layer with a relatively low peel strength for removably contacting the skin and a second layer having a relatively high peel strength for contacting the membrane. In addition, a scrim may be disposed between the second adhesive first and second layers.

In yet another embodiment of the present invention, a fastener includes a first adhesive which has a first layer having a relatively low peel strength for removably contacting the article and a second layer having a relatively high peel strength for contacting the membrane. In addition, a scrim may be disposed between the first adhesive first and second layers.

Preferably, in accordance with the present invention, the first adhesive may have a faster drying rate when exposed to air than a drying rate of the second adhesive. Thus, while the second adhesive does not dry out and affect its adhesion properties with the skin, the drying of the first adhesive facilitates the bonding of the fastener to the article after a period of time. Such first hydrogel adhesives are in the teachings of U.S. Pat. Nos. 4,750,482, 5,143,071, 6,115,625 and 6,347,246 and can be made by relative humectant reduction of compositions herein. The drying rate is changed by variation of the amount of humectant.

BRIEF DESCRIPTION OF THE DRAWINGS

The advantages and features of the present invention will be better understood by the following description when considered in conjunction with the accompanying drawings in which.

DETAILED DESCRIPTION

Figure 1:
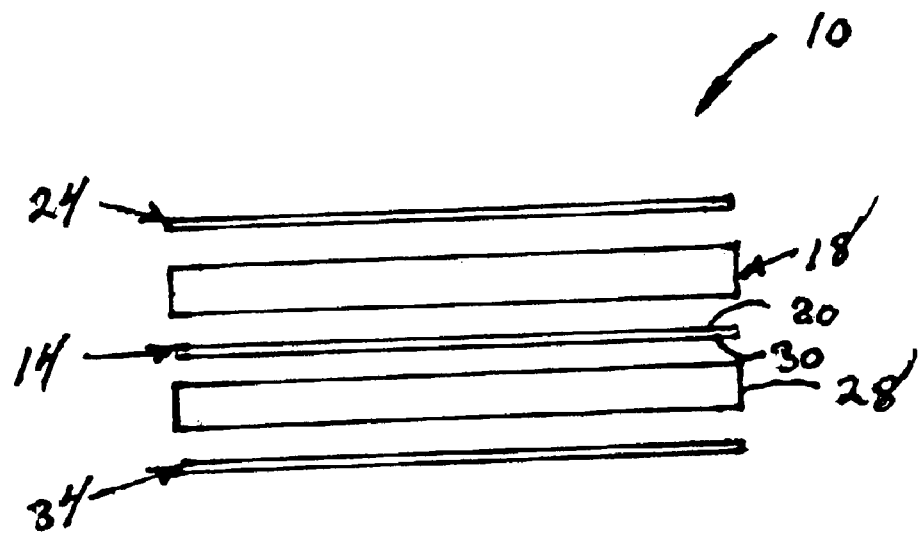
FIG. 1 is an exploded diagram of a dermal fastener in accordance with the present invention generally showing a membrane and a first and second adhesive along with release layers.

With reference to FIG. 1 there is shown a dermal fastener 10 in accordance with the present invention which generally includes a membrane 14 which may be a thermoplastic elastomer having a thickness of between about 0.1 mils and 10 mils. A first adhesive 18 is disposed on one side 20 of the membrane 14 for adherence to an article, not shown. A protective and removable liner 24 may be provided for covering the first adhesive 18 during storage and prior to use. The first and second adhesives may be the same, alternatively, the first adhesive may be any suitable gel or glue, such as, for example, thermoplastic rubber based adhesive or thermoplastic acrylic such as Scapa SP457E and/or UV cure acrylic adhesive. Thicknesses of the first adhesive may be between about 0.5 mils and about 50 mils.

A second adhesive 28 is disposed on another side 30 of the membrane 14 which is covered by a removable liner 34 for protection prior to use and for storage of the fastener 10. The second adhesive 28 is a sheet of film of an organic. polymer plasticized with a polyhydric alcohol, preferably glycerol.

When the first and second adhesives are of the same general composition as set forth herein, the drying rate can be controlled by the relative amounts of humectant utilized used in each adhesive. In this instance the membrane 14 may be eliminated.

The organic polymers that are utilized in preparing the second adhesive 28 are derived from the copolymerization of a mixture of monomeric acrylic acid and a glycolvinylether. Said organic polymer may comprise 10 to 75 parts per hundred, by weight (pph), e.g., 30 to 60 pph, acrylic acid and 75 to 25 pph, e.g. 70 to 40 pph, of a glycolvinylether. In addition, the above mixture of comonomers, the organic polymer, may further include additional comonomers; in particular, the acrylic acid may be completely or partially replaced with AMPS.

Preferably the glycolvinylether may be selected from the group consisting of hydroxybutyl vinyl ether ethyleneglycolvinylether, diethyleneglycolmonovinylether, and triethyleneglycolmethylvinylether. Most preferably the glycolvinyl ether is diethylene glycol monovinyl ether.

Furthermore, the organic polymer may comprise about 0.01 to 1.5 pph of a crosslinking agent, such as methylene bisacrylamide, to increase the molecular weight and cohesivity of the conductive organic polymer through crosslinking. Other comonomers having at least two copolymerizable olefinic moieties, especially difunctional or trifunctional derivatives of acrylic acids, may be utilized. For example, polyethylene glycol dimethacrylates and diacrylates having a molecular weight of from about 200 to about 600 and ethoxylated trimethylolpropane triacrylate (ETMPTA) are preferred crosslinking agents.

The comonomer mixture that is copolymerized to provide the conductive organic polymer will also include a polyhydric alcohol, e.g., polyhydroxyhydrocarbons and oxyalkyls, e.g., polyethylene glycol, sorbitol, glycerol, etc. to plasticize the organic polymer. The polyhydric alcohol functions as a humectant, i.e., it absorbs moisture and promotes conductivity of the adhesive 28. The polyhydric alcohol may comprise from 25 to 75 pph, preferably from 40 to 60 pph, e.g., about 37 to 53 pph of the comonomer mixture. Most preferably, the polyhydric alcohol is glycerol.

The comonomer mixture that is copolymerized to provide the conductive organic polymer may also include a tacky thickening agent. The tacky thickening agent may be a high molecular weight polymer or copolymer such as a N-vinylpyrrolidone/vinylacetate copolymer (Luviskol VA 73W or VA 64w) available from BASF; methylvinylether/maleic anhybrid copolymer (Gantreze® S95), which is available from ISP; ethylene/maleic anhydride (EMA) Copolymer, which is available from Zeeland Chemical; and N-vinylpyrrolidone/acrylic acid Acrylidone® (ACP-1041 or Acrylidone 1005), which is available from ISP, and may comprise from about 0.5 to 8 pph of the comonomer mixture, e.g., about 2 to 5 pph. The N-vinyl pyrrolidone/vinylacetate copolymer disclosed above is especially preferred for use in the adhesives of this invention.

The above comonomer mixture is preferably copolymerized or cured by thermal or ultraviolet (UV) radiation. Therefore, an ultraviolet sensitive curing agent is provided in the comonomer mixture at a concentration of from 0.05 to 3 pph, preferably from 0.5 to 2.0 pph. Suitable curing agents are 2-hydroxy-2 methyl-1-phenyl-propan-2-one (available as Darocur 1173®), 4-(2-hydroxyethoxy)phenyl (2-hydroxy-2-phenyl 2-hydroxy-2-propyl)ketone (available as Darocure 2959™), 2,2-dimethoxy-2-phenyl acetophenone (available as Irgacure® 651), 1-[4-(2-Hydroxyethoxy)-phenyl]-2-hydroxy-2-methyl-1-propane-1-one (available as Irgacure® 2959) or 1-hydroxycyclohexylphenylketone (available as Irgacure 184), all of which are available from Ciba-Geigy and trimethyl benzoyl diphenyl phosphine oxide (available as Esacure DP250).

Thus, to prepare the second adhesive 28, the following gelled comonomer mixtures may be subjected to thermal or ultraviolet polymerization conditions:

| Ingredient | Broad Range pph | Preferred Range pph |
|---|---|---|
| acrylic acid | 2–20 | 4–12 |
| glycolvinylether | 2–20 | 3–10 |
| crosslinker | 0.01–3 | 0.01–2.0 |
| thickener | 0–8 | 0–3.0 |
| glycerin | 25–75 | 35–60 |
| UV sensitive curing agents | 0.5–3 | 0.5–1.5 |
| distilled water | 10–40 | 15–30 |

The acrylic acid is preferably partially neutralized with a basic potassium or sodium oxide, hydroxide, or carbonate or amine, e.g. triethanolamine. For example, from 25 to 75 molar percent acrylic acid may be neutralized.

A buffer may also be included in the comonomer mixture, e.g. from 0.2 to 2 pph of potassium sodium tartrate, or aluminum potassium sulfate (a further function of the $AL^{+3}$ ion of the above buffer and $Mg^{+2}$ ions, as well, is that such ions function as firming agents for the compositions of this invention).

Finally, an aldehyde reactant or neutralization agent may be included to remove any aldehyde generated by the acid hydrolysis of the vinyl ether monomer. Suitable aldehyde reactants include hydrogen peroxide, e.g. from about 1 to 3 pph; 2-hydroxyethylethylene urea, e.g. from about 1 to 5 pph; and L-arginine hydrochloride, e.g. from about 1 to 5 pph. Most preferably the aldehyde reactant is 2-hydroxyethylethylene urea from 3 to 5 pph.

The above conductive substrate has a capacity for absorbing and retaining large amounts of water.

As previously mentioned, while the above disclosed substrate will absorb large amounts of water, it is substantially insoluble in water because the conductive organic polymer contains at least 0.02 parts by weight per 100 parts of monomer of a crosslinking agent.

The adhesive 28 compositions exhibit a tackiness which can be increased as the glycerol concentration is increased. As water and/or salt water is absorbed, the surface of the adhesive 28 softens. As a result, the adhesive 28 will flow into pores and other irregularities in the skin, creating a mechanical interlock bond with the skin in addition to the already present adhesive bond. The bonding is enhanced as it "ages" in contact with the skin.

Importantly, the flexibility and elasticity of the substrate imparted by the glycol vinyl ether co-monomer make it appear that the adhesive 28 never dries out. Actually, the water content does go up and down with the ambient humidity but it is not apparent to the user because the physical properties remain relatively unchanged. Enough water is retained that the fastener remains adhesively functional even in dry conditions for months or years as hereinafter reported.

The UV free radical polymerization reaction of acrylic acid and glycol vinyl ether is so strongly driven that relatively large amounts of glycerol can be incorporated compared to other Uv cure hydrogels. [Also the acrylic acid can be completely reacted in the presence of glycerol if the proper amounts of glycol vinyl ether and UV initiator are used.] This is to be compared with prior art adhesives which typically contain about 20%–40% water and little or no glycerol causing drying to occur within hours.

Figure 2:
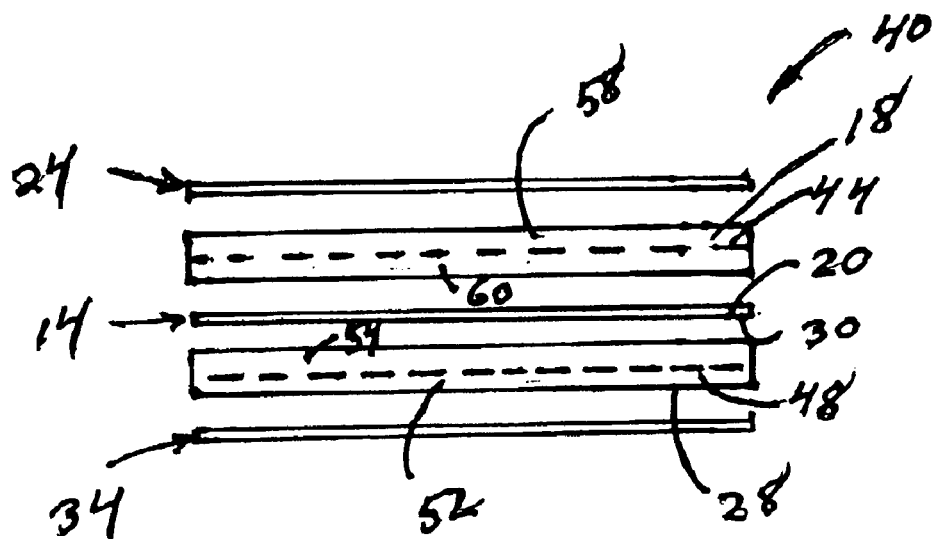
FIG. 2 is an exploded diagram of another embodiment of a dermal fastener in accordance with the present invention similar to that shown in FIG. 1 illustrating the use of scrims in the first and second adhesives.

An alternative embodiment 40 of a fastener in accordance with the present invention is illustrated in FIG. 2 with common reference characters representing identical or substantially similar components as discussed in connection with the embodiment 10 shown in FIG. 1.

The fastener 40 includes scrims 44, 48 disposed within either one or both of the first adhesive 18 and second adhesive 28 respectively. The scrims 44, 48 may be utilized in fastener configurations where a greater thickness of adhesive substrates 18, 28 are preferred. The scrims 44, 48 may be a woven or non-woven spun-bonded polyester fibric, a net of stretched, embossed melt-extruded polymeric film, a sheet of polyolefin monofilaments heat-sealed together at their interstices, a breathable sheet of thermoplastic polymer with holes, heat-stamped in a geometric pattern or any other support or medium. The scrims 44, 48 may be of a material allowing transmission of a light if necessary for curing should the adhesives be cured from one side only. The thickness of the first adhesive 18 and the second adhesive 28 may be between about 0.5 mils and about 50 mils respectively.

In this embodiment 40, the second adhesive may include a first layer 52 having a relatively low peel strength for removably contacting skin (not shown) and a second layer 54 having a relatively high peel strength for contacting the membrane 14. The peel strengths of the layers 52, 54 of the adhesive 28 are improved by increasing acrylic acid content, humectant content, and tacky thickener content. The peel strength of layers 52, 54 of the adhesive 28 are notably reduced by increasing glycolvinylether, crosslinker and water contents.

The use of the scrim 48 facilitates the layering of the first adhesive.

Similarly, the first adhesive 18, 28 may include a first layer 58 having a relatively low peel strength for removably contacting the article and a second layer 60 having a relatively high peel strength for contacting the membrane 14. These peel strengths may be controlled by increasing acrylic acid content, humectant content, and tacky thickener content for increased adhesion and increasing glycovinylether, crosslinker, and water content for adhesion reduction.

It should be appreciated that the first and second adhesives 18, 28 may be configured so that the first adhesive has a faster drying rate, when exposed to air, than the drying rate of the second adhesive. By adjusting the drying rate of the first adhesive utilized to contact an article, the tack of the gel may increase quickly for permanent bonding or slowly to assure that the article remain removable therefrom in order for repositioning or replacement of the fastener 10, 40.

Permanent bonding is desired when the article is discarded after one or a few uses, such as, for example, but not limited to a feeding tube or a clothing item. Temporary bonding is desired when the article is non-disposable, such as, for example, but not limited to a medical device or a prosthesis. As hereinabove noted, the second adhesive is very stable and does not dry out for a very long period of time in order that its effectiveness in being removably attached to the skin is not degraded.

While the second adhesive may be utilized over and over for contacting a person's skin, the fastener should not be utilized to the point where contamination may be detrimental to the skin, such contamination being caused by, for example, dead skin particles or dust, dirt or other foreign particles which may be inadvertently trapped between the fastener and the skin.

The invention is further illustrated by the following example.

EXAMPLE I

Acrylic acid and glycol vinyl ethers copolymerize via a charge transfer complex wherein the vinyl ether acts as an electron donor and the acrylic acid acts as an electron acceptor. This reaction occurs in a matter of minutes if just these two materials are mixed together generating very low molecular weight species; however, high molecular weight species (>10,000) can be created with a free radical initiator. Molecular weights should be greater than about 100,000 daltons to be adhesive and leggy and less than about 5,000,000 daltons, as a higher molecular weight may be too firm at the level of crosslinking preferred. Mixing and curing of the ingredients, utilized in the below examples, must be done quickly to avoid the generation of a significant concentration of aldehydes from the acid hydrolysis of the vinyl ether by the acrylic acid and to avoid generation of low molecular species by autopolymerization.

The adhesive formulation in accordance with the present invention is prepared as follows: Into a stainless steel mixing container, equipped with a mechanical stirrer, is added 62.4 g of deionized water. With slow agitation, 3 g of sodium hydroxide and 6 g of potassium chloride are slowly added to the water. After allowing the stirred caustic solution to cool to room temperature, 48 g acrylic acid, 24 g of diethyleneglycolmonovinylether, 150 g of glycerin and 2.7 g of a 1% solution of methylene-bisacrylamide, in that order, are slowly added to the water containing solution. The resulting mixture is stirred for an additional 15 minutes while the solution is purged with a slow stream of nitrogen gas to displace the residual dissolved oxygen gas from the solution. Finally, a mixture of 0.9 g of CN 383 and 3 g of Irgacures® 184 is poured into the stirred water containing solution. The resulting mixture is coated on and penetrates a polyester scrim, such as Reemay® 1006 or 2250 to provide a coating thickness between 10 to 100, preferably 10–50 mils. Typical line speeds for the coating process vary from 10 to 100, e.g., 30 to 60 linear feet per minute. The coated polyester scrim is irradiated with ultraviolet radiation from a UV source, such as the electrodeless microwave energy activated curing system available as the I-600-M from Fusion Systems Corporation operating at from 400 to 600 watts/inch.

The cured composition is subject to testing for adhesivity (i.e., the bond between the scrim reinforced gel and a substrate, e.g., a standard stainless steel plate or possibly the Mylar® film web upon which the scrim reinforced gel is coated prior to being irradiated), using the Satec T1000 material Testing Machine (SATEC Systems, Grove City, Pa.) equipped with an adjustable tilt table set for 90°. The test procedure for 90° peel strength requires the pulling of a one-inch-wide strip of gel from the substrate (stainless steel plate or Mylar® web) at 12 inches/minute and at an angle of 90' to the plane of the sample as per ASTM D1876, ASTM D3330M (American Society for Testing Materials, Philadelphia, Pa.) or PSTC-1 and -3 (Pressure Sensitive Tape Council, Glenview, Ill.), and recording the average peel force in grams/one inch-width. (ASTM D3330M and PSTC-1 and -3 are for 180° peel testing but were adapted for use in this Example.)

The formulations of Table 1 are prepared similarly, except that various different ingredients may be utilized as specifically noted in Table 1.

Certain of the ingredients (components) of the formulations of Table 1 are as follows:

| | |
|---|---|
| Irgacure ® 2959 | Photoinitiator available from Ciba Specialty Chemicals |
| SR-9035 | 15-mole ethoxylated trimethylol propane triacrylate (ETMPTA) from Sartomer |
| Actilane 755 | Amine synergists available from Akzo Nobel Chemicals America |
| Actilane 705 | |
| CN 373 | Reactive amine coinitiators available from Sartomer |
| CN 383 | |
| SR 511 | 2-Hydroxyethylethylene urea available From Sartomer |
| Hawaiian Blue | Available from Chefmaster ® |
| FA1Q80BC | Acryloxyethyl dimethyl ammonium Chloride available from Ciba |
| Neodox ™ 25-11 | Alcohol ethyl carboxylate available From Hickson DanChem |
| ESACURE DP-250 | Photoinitiator Mixture available from Lamberti |

The compositions of the present invention are suitable for fabricating a dermal fastener that accomplishes the objects of this invention, i.e. the compositions of Table I are soft hydrogels, adhesive to human skin, and having the requisite flexibility and elasticity. The compositions of Table 1 are softer, low in adhesion, and leggy as compared to similar compositions without a glycol vinyl ether component.

As an example, composition 51–30 was evaluated in a Texture Analyzer Study as described in TA, XT 2i Texture Analyzer Study: Sealants & Caulking for Bath and Kitchen Study #I-92 available from Texture Technologies Corp. of Searsdale, N.Y., which is hereby incorporated by reference and made a part of this specification. The results are shown in FIG. 3.

The Texture Analyzer is a probe that pushes into the gel then pulls out of the gel. The graphs are plots of Force vs. time. The first peaks $A^1$, $A^2$, $A^3$, $A^4$ represent the force of resistance to compression and the areas under the peaks represent the compressive work done to penetrate 40% of the gel thickness. The second peaks $B^1$, $B^2$, $B^3$, $B^4$ under the baseline are the maximum adhesive forces and the areas under the peaks represent the adhesive work. If there are two adhesive peaks, the gel is yielding (narrowing and possibly stringing). When the gel lets go, the plots go back to baseline.

Figure 3:
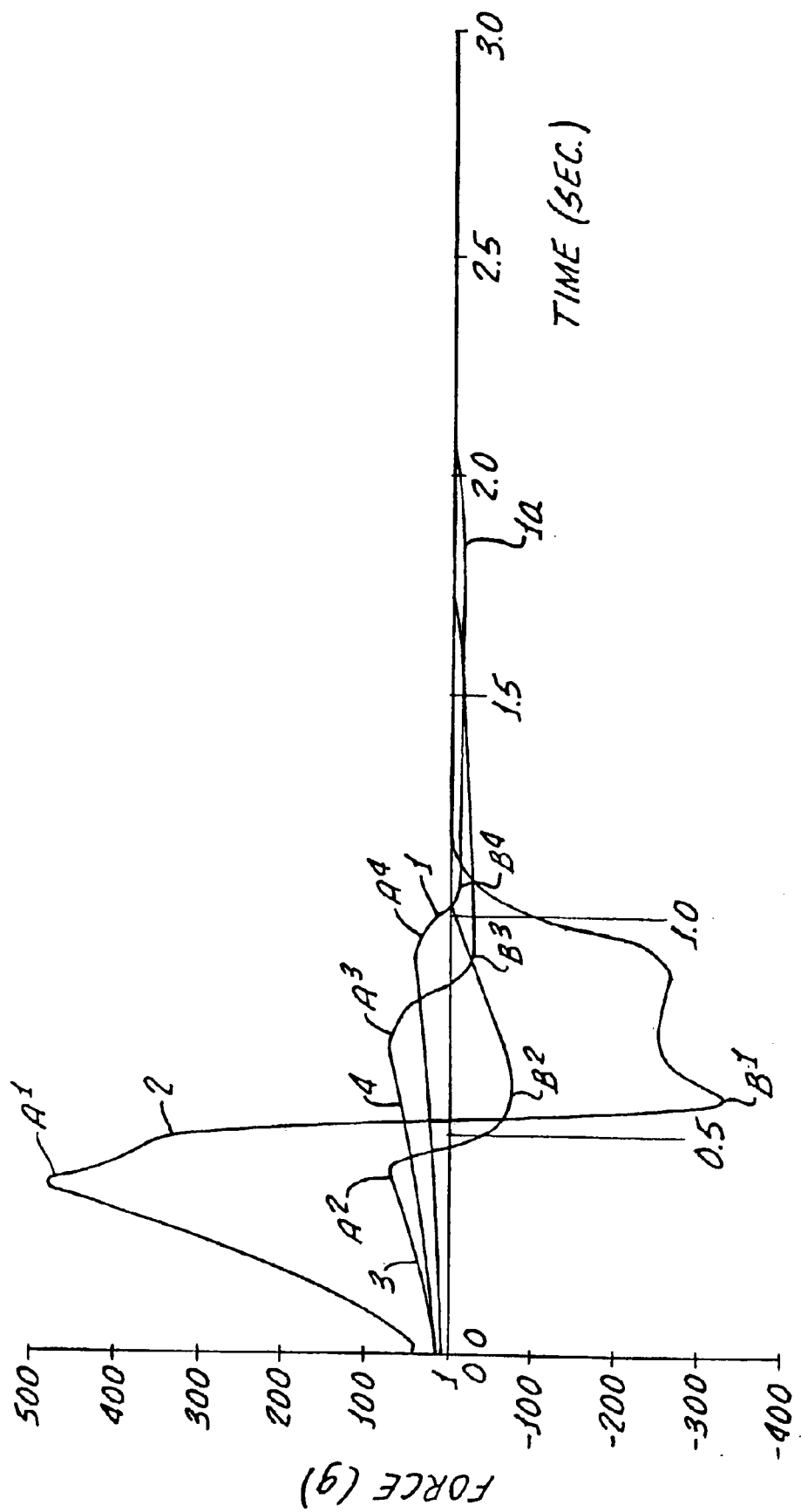
FIG. 3 is a texture analysis plot.

In FIG. 3, a composition (51–30) of this invention (plot 1) is compared to on acrylate copolymer gel comprising a sodium salt of 2-acrylamido propane sulfonic acid and sodium salt of acrylic acid (plot 2). As compared to the pure acrylate gel, the composition of this invention is softer, as shown by the smaller late peak, which is the compression force peak, lower in adhesion, as shown by the small flat peak, and leggy, as shown by the time of release i.e. it holds onto the probe the longest, see plot segment 1a. The composition of this invention rolls off the probe in a wave without yielding.

Also shown in FIG. 3 is plot 3 representing composition 51–97, (no DEGMVE) and plot 4 representing a polyvinyl pyrrolidone adhesive available from Valley Lab, Inc. As shown both plots 3 and 4 have a greater and shorter peak $A^2 A^3$ and peaks $B^2$, $B^3$.

EXAMPLE II

The compositions designated 23–38A in Table I, above, was tested for biocompatibility in the following tests:

An in vitro biocompatibility study, based on the United States Pharmacopeia (USP) guidelines, was conducted on a test article, i.e. Composition 23–38, to determine the potential for cytotoxicity. A 1.0 $cm^2$ portion of the test article, the negative control, and the positive control were each placed on duplicate agarose surfaces directly overlaying confluent monolayers of L-929 mouse fibroblast cells. After incubating at 37° C. in 5% $CO_2$ for 24–26 hours, the cell cultures were examined macroscopically for cell decolorization around the test article and controls to determine the zone of cell lysis (if any). The cultures were then examined microscopically (100×) to verify any decolorized zones and to determine cell morphology in proximity to and beneath the test and control articles.

Under the conditions of this study, the test article showed no evidence of causing cell lysis or toxicity. The test article met the requirements of the USP. The negative and positive controls performed as anticipated.

The test article, Composition 23–38A, was evaluated for primary skin irritation in accordance with the guidelines of the International Organization for Standardization 10993: Biological Evaluation of Medical Devices, Part 10: Tests for Irritation and Sensitization. Two 25 mm×25 mm sections of the test article and control article were topically applied to the skin of three rabbits and left in place for 24 hours. The sites were graded for erythema and edema at 1, 24, 48 and 72 hours after removal of the single sample application.

Under the conditions of this study, no irritation was observed on the skin of the rabbits. The Primary Irritation Index for the test article was calculated to be 0.0. The response of the test article was categorized as negligible.

A study was conducted in the guinea pig to evaluate the potential for delayed dermal contact sensitization of Composition 23–38A. The study was conducted based on the requirements of the International Organization for Standardization 10993: Biological Evaluation of Medical Devices, Part 10: Tests for Irritation and Sensitization.

The test article was occlusively patched for 6 to 8 hours to the intact skin of 10 guinea pigs, three times a week, for a total of nine induction treatments over a 3 week period. The control article was similarly patched to 5 guinea pigs. Following a recovery period, the 10 test and 5 control animals received a challenge patch of the test article and the control article. All sites were observed for evidence of dermal reactions at 24, 48, and 72 hours after patch removal.

Under the conditions of this study the test article showed no evidence of causing delayed dermal contact sensitization in the guinea pig.

It is well known that acrylic gels in general do not perform adequately in the above tests particularly cytotoxicity. (R. Schwalm, et al., "Vinyl Ethers in UV Curing: Copolymers With Acrylates and Unsaturated Polyesters"; Conf. Proc Rad Tech Europe 99; Berlin, Germany; Nov. 8–10, 1999, p 103–109)

The acrylic acid-glycol vinyl ether gels of the present invention achieve perfect scores in the above tests.

In human wear testing on 20 persons (10 male, 10 female) no skin reaction was noted. Three of test subjects have been sensitized to acrylic hydrogel, and experienced no skin reaction to the present invention.

In addition, the gels of present invention have no apparent drying after exposure to the atmosphere between a few days and up to about at least 3 years or longer.

It is noted that the biggest problem that had to be overcome in preparing the above Examples was vinyl ether monomer hydrolysis. There is little basic hydrolysis but there is neutral and substantial acidic hydrolysis with acidity determining the rate. This presented a major impediment when acrylic acid was utilized as a comonomer with a glycol vinyl ether since acrylic acid polymerization is more effective as the pH is lowered. (See U.S. Pat. No. 5,352,713 at column 5, lines 10 and 11, wherein it is stated that acid moieties react with vinyl ethers even in non-water containing systems such as the free radical co-polymerized acrylate-vinyl ether polymer coatings disclosed therein.) Thus, the polymerization reaction is carried out, preferably, at a pH of from about 3.5 to 5.5 to yield a gel having a pH of from about 3.8 to 6.7.

While particular embodiments of the invention have been described, it will be understood, of course, that the invention is not limited thereto since many obvious modifications can be made and it is intended to include within this invention any such modifications as will fall within the scope of the appended claims. For example, it will be appreciated, by those skilled in the art that other alkaline materials can be utilized to neutralize the acrylic acid monomer, e.g., mono and poly positive alkaline materials, e.g., sodium, potassium, calcium, magnesium, aluminum basic oxides, hydroxides or carbonates may be used as well as ammonium hydroxide, etc.

Other thickeners or viscosity increasing agents which may be used in the dermal fasteners of the present invention include polyacrylamide, polyvinyl alcohol, polyacrylic acid, polyethylene oxide, methyl cellulose, ethyl cellulose, carboxymethyl cellulose, hydroxyethyl cellulose and polyacrylamide-alkylsulfonic acid.

Finally, the polymer may include particulate reinforcing agents and/or fillers, such as silica, e.g. Cabosil®.

Although there has been hereinabove described a specific dermal fastener in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclosed herein. Accordingly, any and all modifications, variations or equivalent arrangements which may occur to those skilled in the art, should be considered to be within the scope of the present invention as defined in the appended claims.

What is claimed is:

1. A dermal fastener comprising:
   a membrane;
   a first adhesive, disposed on one side of said membrane, for adherence to an article; and
   a second adhesive, disposed on another side of said membrane, for adherence to skin, said second adhesive comprising a non-liquid water containing film including an organic polymer plasticized with a polyhydric alcohol with said organic polymer being derived from a monomeric mixture comprising from about 2 to about 30 pph acrylic acid, about 2 to about 30 pph of a glycolvinylether, and about 0.01 to about 1.5 pph of a crosslinking agent.

2. The fastener according to claim 1 wherein said polyhydric alcohol is glycerol.

3. The fastener according to claim 2 wherein said crosslinking agent is selected from the group consisting of methylene bis-acrylamide and polyethylene glycol diacrylates and dimethacrylates having a molecular weight from about 200 to about 600.

4. The fastener according to claim 2 wherein said cross linking agent is ETMPTA.

5. The fastener according to claim 1 wherein said glycolvinylether is selected from the group consisting of hydroxybutylvinylether, ethyleneglycolvinylether, diethylene glycol vinylether, and triethyleneglycolmethylvinylether.

6. The fastener according to claim 5 wherein said glycolvinylether is diethylene glycol vinyl ether.

7. The fastener according to claim 5 wherein said monomeric mixture further comprises from about 35 to 60 pph of glycerol.

8. The fastener according to claim 7 wherein at least a portion of said acrylic acid is replaced with 2-acrylamido propane sulfonic acid (AMPS) or a cationic acrylic ester.

9. The fastener according to claim 1 wherein said monomeric mixture further comprises from 0.05 to 3 pph of ultraviolet sensitive curing agents.

10. The fastener according to claim 9 wherein said ultraviolet sensitive curing agent is selected from the group consisting of 2-hydroxy-2-methyl-1-phenylpropan-2-one, 4-(2-hydroxyethoxy)phenyl (2-hydroxy-2-phenyl-2-hydroxy-2-propyl)ketone, 2,2-dimethoxy-2-phenylacetophenone 1-[4-(2-Hydroxyethoxy)-phenyl]-2-hydroxy-2-methyl-1-propane-1-one, 1-hydroxycyclohexylphenyl ketone, trimethyl benzoyl diphenyl phosphine oxide and mixtures thereof.

11. The fastener according to claim 10 wherein said mixture comprises from 5 to 25 pph acrylic acid and from 5 to 25 pph of a glycolvinylether.

12. The fastener according to claim 11 wherein said glycolvinylether is selected from the group consisting of hydroxybutylvinylether, ethyleneglycolvinylether, diethylene glycol vinylether, and triethyleneglycolmethylvinylether.

13. The fastener according to claim 12 wherein said glycol vinylether is diethylene glycol vinyl ether.

14. The fastener according to claim 1 wherein said monomeric mixture further comprises an aldehyde reactant or neutralizer.

15. The fastener according to claim 14 wherein said aldehyde reactant or neutralizer is selected from the group consisting of hydrogen peroxide, hydroxyethylethylene urea and L-arginine hydrochloride.

16. The fastener according to claim 15 wherein said aldehyde reactant or neutralizer is 2-hydroxyethylethylene urea.

17. The fastener according to claim 1 wherein said second adhesive comprises a first layer having a relatively low peel strength for removably contacting the skin and a second layer having a selectively high peel strength for contacting said membrane.

18. The fastener according to claim 17 further comprising a scrim disposed between the second adhesive first and second layer.

19. The fastener according to claim 17 wherein said first adhesive comprises a first layer having a relatively low peel strength for removably contacting the article and a second layer having a relatively high peel strength for contacting said membrane.

20. The fastener according to claim 19 further comprising a scrim disposed between the first adhesive first and second layer.

21. The fastener according to claim 1 wherein said first adhesive has a faster drying rate, when exposed to air, than a drying rate of said second adhesive.

22. A dermal fastener comprising:

a membrane;

a first adhesive, disposed on one side of said membrane, for adherence to an article; said first adhesive comprising a non-liquid water containing film including an organic polymer plasticized with a polyhydric alcohol (humectant) with said organic polymer being derived from a monomeric mixture comprising from about 2 to about 30 pph acrylic acid, about 1 to about 30 pph of glycovinylether, and about 0.01 to about 1.5 pph of a crosslinking agent; and a second adhesive, disposed on another side of said membrane, for adherence to skin, said second adhesive comprising a non-liquid water containing film including an organic polymer plasticized with a polyhydric alcohol (humectant) with said organic polymer being derived from a monomeric mixture comprising from about 2 to about 30 pph acrylic acid, about 1 to about 30 pph of a glycovinylether, and about 0.01 to about 1.5 pph of a crosslinking agent.

23. The dermal fastener according to claim 22 wherein said first adhesive is formulated to have a faster drying rate than said second adhesive in order to permanently bond said dermal fastener to said article.

24. The dermal fastener according to claim 22 wherein the first and second adhesives have drying rates to facilitate removable adhesion to both said article and said skin.

25. A dermal fastener comprising:

a first adhesive for adherence to an article, said first adhesive comprising a non-liquid water containing film including an organic polymer plasticized with a polyhydric alchol (humectant) with said organic polymer being derived from a mixture comprising from about 2 to about 30 pph acid, about 2 to about 30 pph of glycolvinylether, and about 0.01 to about 1.5 pph of a crosslinking agent; and a second adhesive for adherence to skin, said second adhesive comprising non-liquid water containing film including an organic polymer plasticized with a polyhydric alcohol (humectant with said organic polymer being derived from a mixture comprising from about 2 to about 30 pph acrylic acid, about 2 to about 30 pph of glycolvinylether, and about 0.01 to about 1.5 pph of a crosslinking agent.

26. The dermal fastener according to claim 25 wherein said first adhesive is formulated to have a faster drying rate than said second adhesive in order to permanently bond said dermal fastener to said article.

27. The dermal fastener according to claim 25 wherein the first and second adhesives have drying rates to facilitate removable adhesion to both said article and said skin.

28. The dermal fastener according to claim 25 wherein the faster drying rate of said first adhesive is provided by varying an amount of humectant present in each of the first and second adhesives.

* * * * *